(12) United States Patent
Hillman et al.

(10) Patent No.: US 6,168,920 B1
(45) Date of Patent: Jan. 2, 2001

(54) EXTRACELLULAR ADHESIVE PROTEINS

(75) Inventors: Jennifer L. Hillman, Mountain View; Henry Yue, Sunnyvale; Neil C. Corley, Mountain View; Karl J. Guegler, Menlo Park; Chandra Patterson, Mountain View, all of CA (US)

(73) Assignee: Incyte Genomics, Inc., Palo Alto, CA (US)

( * ) Notice: Under 35 U.S.C. 154(b), the term of this patent shall be extended for 0 days.

(21) Appl. No.: 09/131,648

(22) Filed: Aug. 10, 1998

(51) Int. Cl.⁷ .............................. C12Q 1/68; C12P 21/06; C12N 15/00; C12N 5/00; C07K 1/00
(52) U.S. Cl. ..................... 435/6; 435/69.1; 435/320.1; 435/325; 530/350; 536/23.1; 536/23.5
(58) Field of Search ........................... 435/6, 320.1, 69.1, 435/325; 530/350; 536/23.1, 23.5

(56) References Cited

FOREIGN PATENT DOCUMENTS

WO 98/31799   7/1998   (WO) .

OTHER PUBLICATIONS

Hillier, L. et al., GenBank Database, Accession No. AA452364, Jun. 1997.
Murray, J. et al., GenBank Database, Accession No. AC004142, Feb. 1998.
Adams, M. et al., GenBank Database, Accession No. AA311108, Apr. 1997.
Taniguchi, H. et al., DDBJ/EMBL/GenBank databases, Accession No. D49802, Jul. 1996.
Naeve, C. et al., BioTechniques, vol. 19, No. 3, pp. 448–453, 1995.
Kroczek, R., J. Chrom., vol. 618, pp. 133–145, 1993.
Studier, F. et al., J. Mol. Biol., vol. 189, pp. 113–130, 1986.
Saiki, R., PCR Protocols, Academic Press, Inc., pp. 13–20, 1990.

*Primary Examiner*—Ponnathapu Achutamurthy
*Assistant Examiner*—Peter P. Tung
(74) *Attorney, Agent, or Firm*—Incyte Genomics, Inc.

(57) ABSTRACT

The invention provides human extracellular adhesive proteins (EXADH) and polynucleotides which identify and encode EXADH. The invention also provides expression vectors, host cells, antibodies, agonists, and antagonists. The invention also provides methods for diagnosing, treating or preventing disorders associated with expression of EXADH.

9 Claims, 3 Drawing Sheets

| Library | Library Description | Abundance | Percent Abundance |
|---|---|---|---|
| TLYMNOT04 | lymphocytes, activated Th1 cells, 6-hr AB | 5 | 0.1660 |
| TLYMNOT03 | lymphocytes, nonactivated Th1 cells | 8 | 0.1341 |
| TLYMNOT01 | periph blood, lymphocytes, non-adher PBMC, 24M | 1 | 0.1076 |
| TLYMNOT06 | lymphocytes, activated Th2 cells, 6-hr AB | 3 | 0.1003 |

FIGURE 2

EXTRACELLULAR ADHESIVE PROTEINS

FIELD OF THE INVENTION

This invention relates to nucleic acid and amino acid sequences of extracellular adhesive proteins and to the use of these sequences in the diagnosis, treatment, and prevention of cancer, immune disorders, and developmental disorders.

BACKGROUND OF THE INVENTION

The surface of a cell is rich in transmembrane proteoglycans, glycoproteins, glycolipids, and receptors. These macromolecules mediate adhesion with other cells and with components of the extracellular matrix (ECM). The ECM is comprised of diverse glycoproteins, polysaccharides, and carbohydrate-binding proteins which are secreted from the cell and assembled into an organized meshwork in close association with the cell surface. The interaction of the cell with the surrounding matrix profoundly influences cell shape, strength, flexibility, motility, and adhesion. These dynamic properties are intimately associated with signal transduction pathways controlling cell proliferation and differentiation, tissue construction, and embryonic development.

Lectins comprise a ubiquitous family of extracellular glycoproteins which bind cell surface carbohydrates specifically and reversibly, resulting in the agglutination of cells. (Reviewed in Drickamer, K. and Taylor, M. E. (1993) Annu. Rev. Cell Biol. 9:237–264.) This function is particularly important for activation of the immune response. Lectins mediate the agglutination and mitogenic stimulation of lymphocytes at sites of inflammation. (Lasky, L. A. (1991) J. Cell. Biochem. 45:139–146; Paietta, E. et al. (1989) J. Immunol. 143:2850–2857.)

Lectins are further classified into subfamilies based on carbohydrate-binding specificity. The galectin subfamily, in particular, includes lectins that bind β-galactoside carbohydrate moieties in a thioldependent manner. (Reviewed in Hadari, Y. R. et al. (1998) J. Biol. Chem. 270:3447–3453.) Galectins are widely expressed and developmentally regulated. Because all galectins lack an N-terminal signal peptide, it is suggested that galectins are externalized through an atypical secretory mechanism. Two classes of galectins have been defined based on molecular weight and oligomerization properties. Small galectins form homodimers and are about 14 to 16 kilodaltons in mass, while large galectins are monomeric and about 29–37 kilodaltons.

Galectins contain a characteristic carbohydrate recognition domain (CRD). The CRD is about 140 amino acids and contains several stretches of about 1–10 amino acids which are highly conserved among all galectins. A particular 6-amino acid motif within the CRD contains conserved tryptophan and arginine residues which are critical for carbohydrate binding. The CRD of some galectins also contains cysteine residues which may be important for disulfide bond formation. Secondary structure predictions indicate that the CRD forms several β-sheets.

Galectins play a number of roles in diseases and conditions associated with cell-cell and cell-matrix interactions. For example, certain galectins associate with sites of inflammation and bind to cell surface immunoglobulin E molecules. In addition, galectins may play an important role in cancer metastasis. Galectin overexpression is correlated with the metastatic potential of cancers in humans and mice. Moreover, anti-galectin antibodies inhibit processes associated with cell transformation, such as cell aggregation and anchorage-independent growth.

Prostate carcinoma tumor antigen 1 (PCTA-1) is a novel galectin implicated in cancer progression. (Su, Z.-Z. et al. (1996) Proc. Natl. Acad. Sci. U.S.A. 93:7252–7257.) PCTA-1 was initially identified as the cell surface antigen recognized by a prostate tumor-directed monoclonal antibody, Pro 1.5. PCTA-1 cDNA is 3.85 kilobases and encodes a 317-amino acid protein of about 35 kilodaltons. PCTA-1 is expressed in invasive prostate carcinomas and early-stage prostate cancers, but not in normal prostate or benign prostatic hypertrophic tissue. In addition, PCTA-1 is shed from the surface of cultured prostate cancer cells into the growth media. Together, these results suggest that detection of PCTA-1 may be useful for early diagnosis of prostate cancer and that levels of PCTA-1 in the circulation may correlate with disease progression. In addition, preliminary studies in mice suggest that the monoclonal antibody Pro 1.5 may itself be an effective therapeutic agent against tumor progression.

Fibronectin is another component of the ECM which binds to specific integrin-family transmembrane receptors. (Reviewed in Alberts, B. et al. (1994) Molecular Biology of the Cell, Garland Publishing, New York, N.Y., pp. 986–987.) Fibronectin is found in insoluble form in connective tissue and at the base of epithelia. Fibronectin is a dimer composed of two rod-shaped subunits joined by disulfide bonds. Each subunit is a multidomain glycoprotein of nearly 2500 amino acids, and each domain consists of smaller repeated modules. The main type of module is called the type III fibronectin repeat, which consists of about 90–100 amino acids which form several β-sheets. The type III repeat is found in at least 45 protein families, most of which are involved in cell adhesion. Some type III repeats contain a specific tripeptide sequence, the RGD motif. This motif mediates the attachment of fibronectin to the integrin receptor. This motif is also found in various other proteins important for cell-cell adhesion and cell-matrix adhesion, including collagen, fibrinogen, and vitronectin.

Fibronectin is involved in a number of important functions including wound healing, blood coagulation, cell adhesion, cell differentiation, cell migration, embryonic development, and tumor metastasis. In addition, the expression of fibronectin is markedly reduced in neoplastically transformed cells. Furthermore, inactivation of both copies of the fibronectin gene causes early embryonic lethality in mice. These knockout mice have multiple morphological defects, including malformation of the notochord, somites, heart, blood vessels, neural tube, and extraembryonic structures.

A novel class of proteins involved in cell adhesion are the leucine-rich repeat proteins. Leucine rich repeats (LLRs) are about 22–28 amino acids in length and are found in various extracellular adhesive glycoproteins. (Rothberg, J. M. et al. (1990) Genes Dev. 4:2169–2187.) LLRs are predicted to form hydrophobic surfaces capable of interacting with membranes. In addition, synthetic LRRs form β-sheet structures and extended filaments. (Gay, N. J. et al. (1991) FEBS Lett. 291:87–91.) These properties are consistent with a role for LRRs in cell adhesion and cell surface interactions.

The discovery of new extracellular adhesive proteins and the polynucleotides encoding them satisfies a need in the art by providing new compositions which are useful in the diagnosis, prevention, and treatment of cancer, immune disorders, and developmental disorders.

SUMMARY OF THE INVENTION

The invention features substantially purified polypeptides, extracellular adhesive proteins, referred to collectively as "EXADH" and individually as "EXADH-1" and "EXADH-2." In one aspect, the invention provides a substantially purified polypeptide comprising an amino acid sequence selected from the group consisting of SEQ ID NO:1, SEQ ID NO:2, and fragments thereof.

The invention further provides a substantially purified variant having at least 90% amino acid identity to at least one of the amino acid sequences selected from the group consisting of SEQ ID NO:1, SEQ ID NO:2, and fragments thereof. The invention also provides an isolated and purified polynucleotide encoding the polypeptide comprising an amino acid sequence selected from the group consisting of SEQ ID NO:1, SEQ ID NO:2, and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO:1, SEQ ID NO:2, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO:1, SEQ ID NO:2, and fragments thereof. The invention also provides an isolated and purified polynucleotide having a sequence which is complementary to the polynucleotide encoding the polypeptide comprising the amino acid sequence selected from the group consisting of SEQ ID NO:1, SEQ ID NO:2, and fragments thereof.

The invention also provides an isolated and purified polynucleotide comprising a polynucleotide sequence selected from the group consisting of SEQ ID NO:3, SEQ ID NO:4, and fragments thereof. The invention further provides an isolated and purified polynucleotide variant having at least 70% polynucleotide sequence identity to the polynucleotide sequence selected from the group consisting of SEQ ID NO:3, SEQ ID NO:4, and fragments thereof. The invention also provides an isolated and purified polynucleotide having a sequence which is complementary to the polynucleotide comprising a polynucleotide sequence selected from the group consisting of SEQ ID NO:3, SEQ ID NO:4, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO:1, SEQ ID NO:2, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention further includes a purified antibody which binds to a polypeptide selected from the group consisting of SEQ ID NO:1, SEQ ID NO:2, and fragments thereof. The invention also provides a purified agonist and a purified antagonist to the polypeptide.

The invention also provides a method for treating or preventing a disorder associated with decreased expression or activity of EXADH, the method comprising administering to a subject in need of such treatment an effective amount of a pharmaceutical composition comprising a substantially purified polypeptide having the amino acid sequence selected from the group consisting of SEQ ID NO:1, SEQ ID NO:2, and fragments thereof, in conjunction with a suitable pharmaceutical carrier.

The invention also provides a method for treating or preventing a disorder associated with increased expression or activity of EXADH, the method comprising administering to a subject in need of such treatment an effective amount of an antagonist of a polypeptide having an amino acid sequence selected from the group consisting of SEQ ID NO:1, SEQ ID NO:2, and fragments thereof.

BRIEF DESCRIPTION OF THE FIGURES AND TABLES

FIGS. 1A and 1B show the amino acid sequence alignment between EXADH-1 (2635136; SEQ ID NO:1) and PCTA-1 (GI 1932712; SEQ ID NO:5), produced using the multisequence alignment program of LASERGENE software (DNASTAR, Madison Wis.).

FIG. 2 shows electronic northern analysis of SEQ ID NO:4 using the LIFESEQ sequence database (Incyte Pharmaceuticals, Palo Alto Calif.).

Table 1 shows the programs, their descriptions, references, and threshold parameters used to analyze EXADH.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"EXADH" refers to the amino acid sequences of substantially purified EXADH obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to EXADH, increases or prolongs the duration of the effect of EXADH. Agonists may include proteins, nucleic acids, carbohydrates, or any other molecules which bind to and modulate the effect of EXADH.

An "allelic variant" is an alternative form of the gene encoding EXADH. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding EXADH include those sequences with deletions, insertions, or substitutions of different nucleotides, resulting in a polynucleotide the same as EXADH or a polypeptide with at least one functional characteristic of EXADH. Included within this definition are polymorphisms which may or may not be readily detectable using a particular oligonucleotide probe of the polynucleotide encoding EXADH, and improper or unexpected hybridization to allelic variants, with a locus other than the normal chromosomal locus for the polynucleotide sequence encoding EXADH. The encoded protein may also be "altered," and may contain deletions, insertions, or substitutions of amino acid residues which produce a silent change and result in a functionally equivalent EXADH. Deliberate amino acid substitutions may be made on the basis of similarity in polarity, charge, solubility, hydrophobicity, hydrophilicity, and/or the amphipathic nature of the residues, as long as the biological or immunological activity of EXADH is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of EXADH which are preferably at least 5 to about 15 amino acids in length, most preferably at least 14 amino acids, and which retain some biological activity or immunological activity of EXADH. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to EXADH, decreases the amount or the duration of the effect of the biological or immunological activity of EXADH. Antagonists may include proteins, nucleic acids, carbohydrates, antibodies, or any other molecules which decrease the effect of EXADH.

The term "antibody" refers to intact molecules as well as to fragments thereof, such as Fab, F(ab')$_2$, and Fv fragments, which are capable of binding the epitopic determinant. Antibodies that bind EXADH polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic EXADH, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5'A-G-T 3'" bonds to the complementary sequence "3'T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding EXADH or fragments of EXADH may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW Fragment Assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding EXADH, by northern analysis is indicative of the presence of nucleic acids encoding EXADH in a sample, and thereby correlates with expression of the transcript from the polynucleotide encoding EXADH.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR). The MEGALIGN program can create alignments between two or more sequences according to different methods, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of EXADH. For example, modulation may cause an increase or a decrease in protein activity, binding characteristics, or any other biological, functional, or immunological properties of EXADH.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding EXADH, or fragments thereof, or EXADH itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of EXADH polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to EXADH. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

The Invention

The invention is based on the discovery of new human extracellular adhesive proteins (EXADH), the polynucleotides encoding EXADH, and the use of these compositions for the diagnosis, treatment, or prevention of cancer, immune disorders, and developmental disorders.

Nucleic acids encoding the EXADH-1 of the present invention were first identified in Incyte Clone 2635136 from the tibial periosteum cDNA library (BONTNOT01) using a computer search, e.g., BLAST, for amino acid sequence alignments. A consensus sequence, SEQ ID NO:3, was derived from the following overlapping and/or extended nucleic acid sequences: Incyte Clones 2635136H1 (BONTNOT01), 485976R6 (HNT2RAT01), 002834R6 and 002834T6 (HMC1NOT01), and 2818607T6 (BRSTNOT14).

In one embodiment, the invention encompasses a polypeptide comprising the amino acid sequence of SEQ ID NO:1. EXADH-1 is 336 amino acids in length and has one potential cAMP- and cGMP-dependent protein kinase phosphorylation site at S132; four potential casein kinase II phosphorylation sites at S24, S164, S242, and S257; and four potential protein kinase C phosphorylation sites at T102, S205, S242, and T253. EXADH-1 has several features characteristic of galectin proteins. The predicted molecular weight of EXADH-1 is about 37.5 kilodaltons, consistent with the size of large monomeric galectins. BLOCKS and PFAM analyses indicate that the region of EXADH-1 from G67 to D174 is similar to galectin CRD. In particular, the conserved tryptophan and arginine residues which are critical for carbohydrate binding are conserved in EXADH-1 at W117 and R122. EXADH-1 contains seven cysteine residues, four of which are in the putative CRD. Furthermore, secondary structure analysis indicates that the N-terminus of EXADH-1 inclusive of the putative CRD is predicted to form several β-sheets. As shown in FIGS. 1A and 1B, EXADH-1 has chemical and structural similarity with human PCTA-1 (GI 1932712; SEQ ID NO:5). In particular, EXADH-1 and PCTA-1 share 28% identity overall and 44% identity within the putative CRD of EXADH-1 from G67 to D174. In addition, sequence alignments among EXADH-1 and nine galectin CRD sequences indicate that EXADH-1 contains at least 46 out of 55 conserved CRD residues in the region from P48 to D174. A fragment of SEQ ID NO:3 from about nucleotide 346 to about nucleotide 375 is useful as a hybridization probe. Northern analysis shows the expression of this sequence in various libraries, at least 62% of which are associated with cancer, cell proliferation, or fetal development and at least 38% of which are associated with the immune response. In particular, 38% of the libraries expressing this sequence are derived from reproductive tissue and 19% are derived from hematopoietic tissue.

Nucleic acids encoding the EXADH-2 of the present invention were first identified in Incyte Clone 2687731 from the lung cDNA library (LUNGNOT23) using a computer search, e.g., BLAST, for amino acid sequence alignments. A consensus sequence, SEQ ID NO:4, was derived from the following overlapping and/or extended nucleic acid sequences: Incyte Clones 2687731H1 (LUNGNOT23), 268773X309F1, 268773X328F1, and 268773X326F1 (HNT2NOT01), 2836031H1 (TLYMNOT03), 3035425H1 (TLYMNOT05), 2929080T6 (TLYMNOT04), 3003158H1 (TLYMNOT06), and 2107346H1 (BRAITUT03).

In one embodiment, the invention encompasses a polypeptide comprising the amino acid sequence of SEQ ID NO:2. EXADH-2 is 70 amino acids in length and has nine potential N-glycosylation sites at N93, N103, N223, N382, N522, N579, N608, N624, and N625; five potential casein kinase 11 phosphorylation sites at S51, T95, S242, T468, and T487; ten potential protein kinase C phosphorylation sites at T42, S173, T470, T487, S540, S544, S551, S568, T610, and S693; and one potential tyrosine kinase phosphorylation site at Y578. EXADH-2 contains a potential RGD cell attachment sequence from R277 to D279. PRINTS analysis indicates that leucine-rich repeat signatures are interspersed throughout the N-terminal half of EXADH-2. PRINTS and PFAM analyses indicate that the regions of EXADH-2 from N521 to K604 and from E226 to Y244 are similar to fibronectin type III repeats. A signal peptide is predicted from M1 to A22. A fragment of SEQ ID NO:4 from about nucleotide 129 to about nucleotide 158 is useful as a hybridization probe. Northern analysis shows the expression of this sequence in various libraries, at least 65% of which are associated with cancer, cell proliferation, or fetal development and at least 35% of which are associated with the immune response. In particular, 41 % of the libraries expressing this sequence are derived from neural tissue and 29% are derived from hematopoietic tissue. FIG. 2 shows the four cDNA libraries in which SEQ ID NO:4 is most abundantly expressed. Abundance refers to the number of times SEQ ID NO:4 appears in each of the libraries listed, and percent abundance refers to the abundance divided by the total number of sequences examined in a given library. Of particular note is that the percent abundance of SEQ ID NO:4 is highest in cDNA libraries derived from lymphocytes. Sixteen other cDNA libraries express SEQ ID NO:4 at levels which range from about 3- to 25-fold lower.

The invention also encompasses EXADH variants. A preferred EXADH variant is one which has at least about 80%, more preferably at least about 90%, and most preferably at least about 95% amino acid sequence identity to the EXADH amino acid sequence, and which contains at least one functional or structural characteristic of EXADH.

The invention also encompasses polynucleotides which encode EXADH. In a particular embodiment, the invention encompasses a polynucleotide sequence comprising a sequence selected from the group consisting of SEQ ID NO:3 and SEQ ID NO:4, which encodes EXADH.

The invention also encompasses a variant of a polynucleotide sequence encoding EXADH. In particular, such a variant polynucleotide sequence will have at least about 70%, more preferably at least about 85%, and most preferably at least about 95% polynucleotide sequence identity to the polynucleotide sequence encoding EXADH. A particular aspect of the invention encompasses a variant of a polynucleotide sequence comprising a sequence selected from the group consisting of SEQ ID NO:3 and SEQ ID NO:4 which has at least about 70%, more preferably at least about 85%, and most preferably at least about 95% polynucleotide sequence identity to a nucleic acid sequence selected from the group consisting of SEQ ID NO:3 and SEQ ID NO:4. Any one of the polynucleotide variants described above can encode an amino acid sequence which contains at least one functional or structural characteristic of EXADH.

It will be appreciated by those skilled in the art that as a result of the degeneracy of the genetic code, a multitude of polynucleotide sequences encoding EXADH, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring EXADH, and all such variations are to be considered as being specifically disclosed.

Although nucleotide sequences which encode EXADH and its variants are preferably capable of hybridizing to the nucleotide sequence of the naturally occurring EXADH under appropriately selected conditions of stringency, it may be advantageous to produce nucleotide sequences encoding EXADH or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding EXADH and its derivatives without altering the encoded amino acid sequences include the production of RNA transcripts having more desirable properties, such as a greater half-life, than transcripts produced from the naturally occurring sequence.

The invention also encompasses production of DNA sequences which encode EXADH and EXADH derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding EXADH or any fragment thereof.

Also encompassed by the invention are polynucleotide sequences that are capable of hybridizing to the claimed polynucleotide sequences, and, in particular, to those shown in SEQ ID NO:3, SEQ ID NO:4 and fragments thereof under various conditions of stringency. (See, e.g., Wahl, G. M. and S. L. Berger (1987) Methods Enzymol. 152:3–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 1.0% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (U.S. Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the Hamilton MICROLAB 2200 (Hamilton, Reno Nev.), Peltier Thermal Cycler 200 (PTC200; MJ Research, Watertown Mass.) and the ABI CATALYST 800 (Perkin-Elmer). Sequencing is then carried out using either ABI 373 or 377 DNA Sequencing Systems (Perkin-Elmer) or the MEGABACE capillary electrophoresis system (Molecular Dynamics, Sunnyvale Calif.). The resulting sequences are analyzed using a variety of algorithms which are well known in the art. (See, e.g., Ausubel, F. M. (1997) *Short Protocols in Molecular Biology,* John Wiley & Sons, New York N.Y., unit 7.7; Meyers, R. A. (1995) *Molecular Biology and Biotechnology,* Wiley VCH, New York N.Y., pp. 856–853.)

The nucleic acid sequences encoding EXADH may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer Analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode EXADH may be cloned in recombinant DNA molecules that direct expression of EXADH, or fragments or functional equivalents thereof, in appropriate host cells. Due to the inherent degeneracy of the genetic code, other DNA sequences which encode substantially the same or a functionally equivalent amino acid sequence may be produced and used to express EXADH.

The nucleotide sequences of the present invention can be engineered using methods generally known in the art in order to alter EXADH-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding EXADH may be synthesized, in whole or in part, using chemical methods well known in the art. (See, e.g., Caruthers, M. H. et al. (1980) Nucl. Acids Res. Symp. Ser. 215–223, and Hom, T. et al. (1980) Nucl. Acids Res. Symp. Ser. 225–232.) Alternatively, EXADH itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431 A Peptide Synthesizer (Perkin-Elmer). Additionally, the amino acid sequence of EXADH, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1984) Proteins. Structures and Molecular Properties, WH Freeman, New York N.Y.)

In order to express a biologically active EXADH, the nucleotide sequences encoding EXADH or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding EXADH. Such elements may vary in their strength and specificity. Specific initiation signals may also be used to achieve more efficient translation of sequences encoding EXADH. Such signals include the ATG initiation codon and adjacent sequences, e.g. the Kozak sequence. In cases where sequences encoding EXADH and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding EXADH and appropriate transcriptional and translational control elements. These methods include in vitro recombinant DNA techniques, synthetic techniques, and in vivo genetic recombination. (See, e.g., Sambrook, J. et al. (1989) Molecular Cloning. A Laboratory Manual, Cold Spring Harbor Press, Plainview N.Y., ch. 4, 8, and 16–17; Ausubel, F. M. et al. (1995) Current Protocols in Molecular Biology, John Wiley & Sons, New York N.Y., ch. 9, 13, and 16.)

A variety of expression vector/host systems may be utilized to contain and express sequences encoding EXADH. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding EXADH. For example, routine cloning, subcloning, and propagation of polynucleotide sequences encoding EXADH can be achieved using a multifunctional *E. coli* vector such as PBLUESCRIPT (Stratagene, La Jolla Calif.) or pSPORT1 plasmid (Life Technologies). Ligation of sequences encoding EXADH into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of EXADH are needed, e.g. for the production of antibodies, vectors which direct high level expression of EXADH may be used. For example, vectors containing the strong, inducible T5 or T7 bacteriophage promoter may be used.

Yeast expression systems may be used for production of EXADH. A number of vectors containing constitutive or inducible promoters, such as alpha factor, alcohol oxidase, and PGH, may be used in the yeast *Saccharomyces cerevisiae* or *Pichia pastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of EXADH. Transcription of sequences encoding EXADH may be driven viral promoters, e.g., the 35S and 19S promoters of CaMV used alone or in combination with the omega leader sequence from TMV. (Takamatsu, N. (1987) EMBO J. 6:307–311.) Alternatively, plant promoters such as the small subunit of RUBISCO or heat shock promoters may be is used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding EXADH may be ligated into an adenovirus transcription/translation complex consisting of the late promoter and tripartite leader sequence. Insertion in a non-essential E1 or E3 region of the viral genome may be used to obtain infective virus which expresses EXADH in host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.) For long term production of recombinant proteins in mammalian systems, stable expression of EXADH in cell lines is preferred. For example, sequences encoding EXADH can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding EXADH is inserted within a marker gene sequence, transformed cells containing sequences encoding EXADH can be identified by the absence of marker gene function. Alternatively, a marker gene can be placed in tandem with a sequence encoding EXADH under the control of a single promoter. Expression of the marker gene in response to induction or selection usually indicates expression of the tandem gene as well.

In general, host cells that contain the nucleic acid sequence encoding EXADH and that express EXADH may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of EXADH using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on EXADH is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York NY; and Pound, J. D. (1998) Immunochemical Protocols, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding EXADH include oligolabeling, nick translation, end-labeling, or PCR amplification using a labeled nucleotide. Alternatively, the sequences encoding EXADH, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and U.S. Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding EXADH may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode EXADH may be designed to contain signal sequences which direct secretion of EXADH through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and W138), are available from the American Type Culture Collection (ATCC, Bethesda Md.) and may be chosen to ensure the correct modification and processing of the foreign protein.

In another embodiment of the invention, natural, modified, or recombinant nucleic acid sequences encoding EXADH may be ligated to a heterologous sequence resulting in translation of a fusion protein in any of the aforementioned host systems. For example, a chimeric EXADH protein containing a heterologous moiety that can be recognized by a commercially available antibody may facilitate the screening of peptide libraries for inhibitors of EXADH activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the EXADH encoding sequence and the heterologous protein sequence, so that EXADH may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled EXADH may be achieved in vitro using the TNT rabbit reticulocyte lysate or wheat germ extract systems (Promega). These systems couple transcription and translation of protein-coding sequences operably associated with the T7, T3, or SP6 promoters. Translation takes place in the presence of a radiolabeled amino acid precursor, preferably $^{35}$S-methionine.

Fragments of EXADH may be produced not only by recombinant production, but also by direct peptide synthesis using solid-phase techniques. (See, e.g., Creighton, supra pp. 55–60.) Protein synthesis may be performed by manual techniques or by automation. Automated synthesis may be achieved, for example, using the ABI 431 A Peptide Synthesizer (Perkin-Elmer). Various fragments of EXADH may be synthesized separately and then combined to produce the full length molecule.

Therapeutics

Chemical and structural similarity exists among regions of EXADH-1, PCTA-1, and sequences conserved among galectins. Chemical and structural similarity also exists among regions of EXADH-2, fibronectin type III modules, and LRRs. In addition, EXADH is expressed in cells and cell lines associated with fetal tissue, cancer, and the immune system. Therefore, EXADH appears to be associated with cancer, immune disorders, and developmental disorders. In the treatment of cancer, immune disorders, and developmental disorders associated with increased EXADH activity, it is desirable to decrease the expression or activity of EXADH. In the treatment of the above conditions associated with decreased EXADH activity, it is desirable to provide the protein or to increase the expression of EXADH. Therefore, in one embodiment, EXADH or a fragment or derivative thereof may be administered to a subject to treat or prevent a disorder associated with decreased expression or activity of EXADH. Such disorders can include, but are not limited to, a cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, e.g., the brain, adrenal gland, kidney, skeletal or reproductive system.

In another embodiment, a vector capable of expressing EXADH or a fragment or derivative thereof may be administered to a subject to treat or prevent a disorder associated with decreased expression or activity of EXADH including, but not limited to, those described above.

In a further embodiment, a pharmaceutical composition comprising a substantially purified EXADH in conjunction with a suitable pharmaceutical carrier may be administered to a subject to treat or prevent a disorder associated with decreased expression or activity of EXADH including, but not limited to, those provided above.

In still another embodiment, an agonist which modulates the activity of EXADH may be administered to a subject to treat or prevent a disorder associated with decreased expression or activity of EXADH including, but not limited to, those listed above.

In a further embodiment, an antagonist of EXADH may be administered to a subject to treat or prevent a disorder associated with increased expression or activity of EXADH. Such disorders may include, but are not limited to, those discussed above. In one aspect, an antibody which specifically binds EXADH may be used directly as an antagonist or indirectly as a targeting or delivery mechanism for bringing a pharmaceutical agent to cells or tissue which express EXADH.

In an additional embodiment, a vector expressing the complement of the polynucleotide encoding EXADH may be administered to a subject to treat or prevent a disorder associated with increased expression or activity of EXADH including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of EXADH may be produced using methods which are generally known in the art. In particular, purified EXADH may be used to produce antibodies or to screen libraries of pharmaceutical agents to identify those which specifically bind EXADH. Antibodies to EXADH may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with EXADH or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to EXADH have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of EXADH amino acids may be fused with those of another protein, such as KLH, and antibodies to the chimeric molecule may be produced.

Monoclonal antibodies to EXADH may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce EXADH-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; Winter, G. et al. (1991) Nature 349:293–299.)

Antibody fragments which contain specific binding sites for EXADH may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between EXADH and its specific antibody. A two-site, monoclonal-based immunoassay utilizing monoclonal antibodies reactive to two non-interfering EXADH epitopes is preferred, but a competitive binding assay may also be employed (Pound, supra).

In another embodiment of the invention, the polynucleotides encoding EXADH, or any fragment or complement thereof, may be used for therapeutic purposes. In one aspect, the complement of the polynucleotide encoding EXADH may be used in situations in which it would be desirable to block the transcription of the mRNA. In particular, cells may be transformed with sequences complementary to polynucleotides encoding EXADH. Thus, complementary molecules or fragments may be used to modulate EXADH activity, or to achieve regulation of gene function. Such technology is now well known in the art, and sense or antisense oligonucleotides or larger fragments can be designed from various locations along the coding or control regions of sequences encoding EXADH.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding EXADH. (See, e.g., Sambrook, supra; Ausubel, 1995, supra.)

Genes encoding EXADH can be turned off by transforming a cell or tissue with expression vectors which express high levels of a polynucleotide, or fragment thereof, encoding EXADH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding EXADH. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding EXADH.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding EXADH. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2'O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of EXADH, antibodies to EXADH, and mimetics, agonists, antagonists, or inhibitors of EXADH. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of EXADH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example EXADH or fragments thereof, antibodies of EXADH, and agonists, antagonists or inhibitors of EXADH, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or LD50 (the dose lethal to 50% of the population) statistics. The dose ratio of therapeutic to toxic effects is the therapeutic index, and it can be expressed as the $ED_{50}/LD_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Longacting pharmaceutical compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind EXADH may be used for the diagnosis of disorders characterized by expression of EXADH, or in assays to monitor patients being treated with EXADH or agonists, antagonists, or inhibitors of EXADH. Antibodies useful for diagnostic purposes may be prepared in the same manner as described above for therapeutics. Diagnostic assays for EXADH include methods which utilize the antibody and a label to detect EXADH in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring EXADH, including ELISAs, RIAs, and FACS, are known in the art and provide a basis for diagnosing altered or abnormal levels of EXADH expression. Normal or standard values for FXADH expression are established by combining body fluids or cell extracts taken from normal mammalian subjects, preferably human, with antibody to EXADH under conditions suitable for complex formation. The amount of standard complex formation may be quantitated by various methods, preferably by photometric means. Quantities of EXADH expressed in subject, control, and disease samples from biopsied tissues are compared with the standard values. Deviation between standard and subject values establishes the parameters for diagnosing disease.

In another embodiment of the invention, the polynucleotides encoding EXADH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of EXADH may be correlated with disease. The diagnostic assay may be used to determine absence, presence, and excess expression of EXADH, and to monitor regulation of EXADH levels during therapeutic intervention.

In one aspect, hybridization with PCR probes which are capable of detecting polynucleotide sequences, including genomic sequences, encoding EXADH or closely related molecules may be used to identify nucleic acid sequences which encode EXADH. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding EXADH, allelic variants, or related sequences.

Probes may also be used for the detection of related sequences, and should preferably have at least 50% sequence identity to any of the EXADH encoding sequences. The hybridization probes of the subject invention may be DNA or RNA and may be derived from the sequence of SEQ ID NO:3 or SEQ ID NO:4 or from genomic sequences including promoters, enhancers, and introns of the EXADH gene.

Means for producing specific hybridization probes for DNAs encoding EXADH include the cloning of polynucleotide sequences encoding EXADH or EXADH derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding EXADH may be used for the diagnosis of disorders associated with expression of EXADH. Examples of such disorders include, but are not limited to, a cancer such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an immune disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderima, Sjogren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, trauma, X-linked agammaglobinemia of Bruton, common variable immunodeficiency (CVI), DiGeorge's syndrome (thymic hypoplasia), thymic dysplasia, isolated IgA deficiency, severe combined immunodeficiency disease (SCID), immunodeficiency with thrombocytopenia and eczema (Wiskott-Aldrich syndrome), Chediak-Higashi syndrome, chronic granulomatous diseases, hereditary angioneurotic edema, and immunodeficiency associated with Cushing's disease; and a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spina bifida, anencephaly, craniorachischisis, congenital glaucoma, cataract, sensorineural hearing loss, and any disorder associated with cell growth and differentiation, embryogenesis, and morphogenesis involving any tissue, organ, or system of a subject, e.g., the brain, adrenal gland, kidney, skeletal or reproductive system. The polynucleotide sequences encoding EXADH may be used in Southern or northern analysis, dot blot, or other membrane-based technologies; in PCR technologies; in dipstick, pin, and ELISA assays; and in microarrays utilizing fluids or tissues from patients to detect altered EXADH expression. Such qualitative or quantitative methods are well known in the art.

In a particular aspect, the nucleotide sequences encoding EXADH may be useful in assays that detect the presence of associated disorders, particularly those mentioned above. The nucleotide sequences encoding EXADH may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding EXADH in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of EXADH, a normal or standard profile for expression is established. This may be accomplished by combining body fluids or cell extracts taken from normal subjects, either animal or human, with a sequence, or a fragment thereof, encoding EXADH, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding EXADH may involve the use of PCR. These oligomers may be chemically synthesized, generated enzymatically, or produced in vitro. Oligomers will preferably contain a fragment of a polynucleotide encoding EXADH, or a fragment of a polynucleotide complementary to the polynucleotide encoding EXADH, and will be employed under optimized conditions for identification of a specific gene or condition. Oligomers may also be employed under less stringent conditions for detection or quantitation of closely related DNA or RNA sequences.

Methods which may also be used to quantitate the expression of EXADH include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding EXADH may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat Genet.

15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding EXADH on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11 q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, EXADH, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between EXADH and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with EXADH, or fragments thereof, and washed. Bound EXADH is then detected by methods well known in the art. Purified EXADH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding EXADH specifically compete with a test compound for binding EXADH. In this manner, antibodies can be used to detect the presence of any peptide which shares one or more antigenic determinants with EXADH.

In additional embodiments, the nucleotide sequences which encode EXADH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

The BONTNOT01 cDNA library was constructed using RNA isolated from tibial periosteum removed from a 20-year-old Caucasian male during a hemipelvectomy with amputation above the knee. Pathology for the associated tumor tissue indicated partially necrotic and cystic osteoblastic grade 3 osteosarcoma, post-chemotherapy. Family history included osteogenesis imperfecta, closed fracture, and type II diabetes.

The LUNGNOT23 cDNA library was constructed using RNA isolated from left lobe lung tissue removed from a 58-year-old Caucasian male. Pathology for the associated tumor tissue indicated metastatic grade 3 (of 4) osteosarcoma. Patient history included soft tissue cancer, secondary cancer of the lung, prostate cancer, and an acute duodenal ulcer with hemorrhage. Family history included prostate cancer, breast cancer, and acute leukemia.

For construction of the BONTNOT01 and LUNGNOT23 cDNA libraries, frozen tissue from each of the above sources was homogenized and lysed in TRIzol reagent (1 gm tissue/ 10 ml TRIzol; Life Technologies), a monophasic solution of phenol and guanidine isothiocyanate, using a Brinkmann Homogenizer Polytron PT-3000 (Brinkmann Instruments, Westbury N.Y.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted as necessary with acid phenol-chloroform to increase purity, and the RNA was reprecipitated with sodium acetate and ethanol.

From each RNA preparation, poly(A+) RNA was isolated using the OLIGOTEX kit (QIAGEN, Chatsworth Calif.). Poly(A+) RNA was used for cDNA synthesis and construction of each cDNA library according to the recommended protocols in the SUPERSCRIPT plasmid system (Life Technologies). The cDNAs were fractionated on a SEPHAROSE CL4B column (Amersham Pharmacia Biotech), and those cDNAs exceeding 400 bp were ligated into pINCY (Incyte Pharmaceuticals). Recombinant plasmids were transformed into DH5α competent cells (Life Technologies).

II. Isolation of cDNA Clones

Plasmid DNA was released from the cells and purified using the REAL Prep 96 plasmid kit (QIAGEN). The recommended protocol was employed except for the following changes: 1) the bacteria were cultured in 1 ml of sterile Terrific Broth (Life Technologies) with carbenicillin at 25 mg/l and glycerol at 0.4%; 2) after the cultures were incubated for 19 hours, the cells were lysed with 0.3 ml of lysis buffer; and 3) following isopropanol precipitation, the plasmid DNA pellets were each resuspended in 0.1 ml of distilled water. The DNA samples were stored at 4° C.

III. Sequencing and Analysis

The cDNAs were prepared for sequencing using either an ABI CATALYSTS 800 (Perkin-Elmer) or a MICROLAB 2200 (Hamilton) sequencing preparation system in combination with PTC-200 thermal cyclers (MJ Research). The cDNAs were sequenced using the ABI PRISM 373 or 377 sequencing systems and ABI protocols, base calling software, and kits (Perkin-Elmer). Alternatively, solutions and dyes from Amersham Pharmacia Biotech were used. Reading frames were determined using standard methods (Ausubel, 1995, supra). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 1 summarizes the software programs, descriptions, references, and threshold parameters used. The first column of Table 1 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, S. San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, PFAM, and Prosite.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch. 4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

sequence identity×% maximum BLAST score/100

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a list of libraries in which the transcript encoding EXADH occurred. Abundance and percent abundance are also reported. Abundance directly reflects the number of times a particular transcript is represented in a CDNA library, and percent abundance is abundance divided by the total number of sequences examined in the CDNA library. Further analyses produced the percentage values of tissue-specific and disease expression which are reported in the description of the invention.

V. Extension of EXADH Encoding Polynucleotides

The nucleic acid sequences of Incyte ESTs 2633156 and 2687731 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" which generates amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PerkinElmer) and thoroughly mixing the enzyme and reaction mix. PCR was performed using the PTC200 thermal cycler (M.J. Research) beginning with 40 pmol of each primer and the recommended concentrations of all other components of the kit, with the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4–6 for an additional 15 cycles |
| Step 8 | 94° C. for 15 sec |
| Step 9 | 65° C. for 1 min |
| Step 10 | 68° C. for 7:15 min |
| Step 11 | Repeat steps 8–10 for an additional 12 cycles |
| Step 12 | 72° C. for 8 min |
| Step 13 | 4° C. (and holding) |

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using the QIAQUICK kit (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the *E. coli* mixture was plated on Luria Bertani (LB) agar (See, e.g., Sambrook, supra, Appendix A, p. 1) containing carbenicillin (2× carb). The following day, several colonies were randomly picked from each plate and cultured in 150 μl of liquid LB/2× carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|--------|-------------------|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:3 and SEQ ID NO:4 are used to obtain 5' regulatory sequences using the procedure above, oligonucleotides designed for 5' extension, and an appropriate genomic library.

VI. Labeling and use of Individual Hybridization Probes

Hybridization probes derived from SEQ ID NO:3 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [γ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba1, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT-AR film (Eastman Kodak, Rochester N.Y.) is exposed to the blots to film for several hours, hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The CDNA is fixed to the slide using, e.g., UV cross-linking followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the EXADH-encoding sequences, or any parts thereof, are used to detect, decrease, or inhibit expression of naturally occurring EXADH. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of EXADH. To inhibit transcription, a complementary oligonucleotide is designed from the most unique 5' sequence and used to prevent promoter binding to the coding sequence. To inhibit translation, a complementary oligonucleotide is designed to prevent ribosomal binding to the EXADH-encoding transcript.

IX. Expression of EXADH

Expression and purification of EXADH is achieved using bacterial or virus-based expression systems. For expression of EXADH in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express EXADH upon induction with isopropyl beta-D-thiogalactopyranoside (IPTG). Expression of EXADH in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding EXADH by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. U.S.A. 91:3224–3227; Sandig, V. et al. (1996) Hum. Gene Ther. 7:1937–1945.)

In most expression systems, EXADH is synthesized as a fusion protein with, e.g., glutathione Stransferase (GST) or a peptide epitope tag, such as FLAG or 6-His, permitting rapid, single-step, affinity-based purification of recombinant fusion protein from crude cell lysates. GST, a 26-kilodalton enzyme from Schistosoma japonicum, enables the purification of fusion proteins on immobilized glutathione under conditions that maintain protein activity and antigenicity (Amersham Pharmacia Biotech). Following purification, the GST moiety can be proteolytically cleaved from EXADH at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified EXADH obtained by these methods can be used directly in the following activity assay.

X. Demonstration of EXADH Activity

An assay for EXADH activity measures the amount of cell aggregation induced by overexpression of EXADH. In this assay, cultured cells such as NIH3T3 are transfected with cDNA encoding EXADH contained within a suitable mammalian expression vector under control of a strong promoter. Cotransfection with cDNA encoding a fluorescent marker protein, such as Green Fluorescent Protein (Clontech), is useful for identifying stable transfectants. The amount of cell agglutination, or clumping, associated with transfected cells is compared with that associated with untransfected cells. The amount of cell agglutination is a direct measure of EXADH activity.

XI. Functional Assays

EXADH function is assessed by expressing the sequences encoding EXADH at physiologically elevated levels in mammalian cell culture systems. cDNA is subcloned into a mammalian expression vector containing a strong promoter that drives high levels of cDNA expression. Vectors of choice include pCMV SPORT (Life Technologies) and pCR3.1 (Invitrogen, Carlsbad Calif.), both of which contain the cytomegalovirus promoter. 5–10 µg of recombinant vector are transiently transfected into a human cell line, preferably of endothelial or hematopoietic origin, using either liposome formulations or electroporation. 1–2 µg of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cytometry, Oxford, New York N.Y.

The influence of EXADH on gene expression can be assessed using highly purified populations of cells transfected with sequences encoding EXADH and either CD64 or CD64-GFP. CD64 and CD64GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding EXADH and other genes of interest can be analyzed by northern analysis or microarray techniques.

XII. Production of EXADH Specific Antibodies

EXADH substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the EXADH amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.) Typically, oligopeptides 15 residues in length are synthesized using an ABI 431 A Peptide Synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring EXADH Using Specific Antibodies

Naturally occurring or recombinant EXADH is substantially purified by immunoaffinity chromatography using antibodies specific for EXADH. An immunoaffinity column is constructed by covalently coupling anti-EXADH antibody to an activated chromatographic resin, such as CNBr-activated SEPHAROSE (Amersham Pharmacia Biotech). After the coupling, the resin is blocked and washed according to the manufacturer's instructions.

Media containing EXADH are passed over the immunoaffinity column, and the column is washed under conditions that allow the preferential absorbance of EXADH (e.g., high ionic strength buffers in the presence of detergent). The column is eluted under conditions that disrupt antibody/EXADH binding (e.g., a buffer of pH 2 to pH 3, or a high concentration of a chaotrope, such as urea or thiocyanate ion), and EXADH is collected.

XIV. Identification of Molecules Which Interact with EXADH

EXADH, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled EXADH, washed, and any wells with labeled EXADH complex are assayed. Data obtained using different concentrations of EXADH are used to calculate values for the number, affinity, and association of EXADH with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S.F. et al. (1990) J. Mol. Biol. 215:403–410; Altschul, S.F. et al. (1997) Nucleic Acids Res. 25: 3389–3402. | ESTs: Probability value = 1.0E – 8 or less Full Length sequences: Probability value = 1.0E – 10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W.R. and D.J. Lipman (1988) Proc. Natl. Acad Sci. 85:2444–2448; Pearson, W.R. (1990) Methods Enzymol. 183: 63–98; and Smith, T.F. and M.S. Waterman (1981) Adv. Appl. Math. 2:482–489. | ESTs: fasta E value = 1.06E – 6 Assembled ESTs: fasta Identity = 95% or greater and Match length = 200 bases or greater; fastx E value = 1.0E – 8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff, S and J.G. Henikoff, Nucl. Acid Res., 19:6565–72, 1991. J.G. Henikoff and S. Henikoff (1996) Methods Enzymol. 266:88–105; and Attwood, T.K. et al. (1997) J. Chem. Inf. Comput. Sci. 37: 417–424. | Score = 1000 or greater; Ratio of Score/Strength = 0.75 or larger; and Probability value = 1.0E – 3 or less |
| PFAM | A Hidden Markov Models-based application useful for protein family search. | Krogh, A. et al. (1994) J. Mol. Biol., 235:1501–1531; Sonnhammer, E.L.L. et al. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25: 217–221. | Score = 4.0 or greater |
| Phred | A base-calling algorithm that examines automated sequencer traces with high sensitivity and probability | Ewing, B. et al. (1998) Genome Res. 8:175–185; Ewing B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T.F. and M.S. Waterman (1981) Adv. Appl. Math. 2:482–489; Smith, T.F. and M.S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res. 8:195–202. | |
| SPScan | A weight matrix analysis program that scans protein sequences for the presence of secretory signal peptides. | Nielson, H. et al. (1997) Protein Engineering 10:1–6; Claverie, J.M. and S. Audic (1997) CABIOS 12: 431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. An isolated and purified polynucleotide encoding a polypeptide comprising the amino acid sequence of SEQ ID NO:1.

2. An isolated and purified polynucleotide having a sequence which is fully complementary to the polynucleotide of claim 1.

3. An isolated and purified polynucleotide comprising the polynucleotide sequence of SEQ ID NO:3.

4. An isolated and purified polynucleotide having a sequence which is fully complementary to the polynucleotide of claim 3.

5. An expression vector comprising the polynucleotide of claim 1.

6. A host cell comprising the expression vector of claim 5.

7. A method for producing a polypeptide, the method comprising the steps of:
   a) culturing the host cell of claim 6 under conditions suitable for the expression of the polypeptide; and
   b) recovering the polypeptide from the host cell culture.

8. A method for detecting a polynucleotide, the method comprising the steps of:
   (a) hybridizing the polynucleotide of claim 2 to at least one nucleic acid in a sample, thereby forming a hybridization complex; and
   (b) detecting the hybridization complex, wherein the presence of the hybridization complex correlates with the presence of the polynucleotide in the sample.

9. The method of claim 8 further comprising amplifying the polynucleotide prior to hybridization.

* * * * *

SEQUENCE LISTING

<160> NUMBER OF SEQ ID NOS: 5

<210> SEQ ID NO 1
<211> LENGTH: 336
<212> TYPE: PRT
<213> ORGANISM: Homo sapiens
<220> FEATURE: -
<223> OTHER INFORMATION: 2635136

<400> SEQUENCE: 1

```
Met Ser Gln Pro Ser Gly Gly Arg Ala Pro Gly Thr Arg Ile Tyr
 1               5                  10                  15

Ser Trp Ser Cys Pro Thr Val Met Ser Pro Gly Glu Lys Leu Asp
                20                  25                  30

Pro Ile Pro Asp Ser Phe Ile Leu Gln Pro Val Phe His Pro
                35                  40                  45

Val Val Pro Tyr Val Thr Thr Ile Phe Gly Gly Leu His Ala Gly
                50                  55                  60

Lys Met Val Met Leu Gln Gly Val Val Pro Leu Asp Ala His Arg
                65                  70                  75

Phe Gln Val Asp Phe Gln Cys Gly Cys Ser Leu Cys Pro Arg Pro
                80                  85                  90

Asp Ile Ala Phe His Phe Asn Pro Arg Phe His Thr Thr Lys Pro
                95                  100                 105

His Val Ile Cys Asn Thr Leu His Gly Gly Arg Trp Gln Arg Glu
                110                 115                 120

Ala Arg Trp Pro His Leu Ala Leu Arg Arg Gly Ser Ser Phe Leu
                125                 130                 135

Ile Leu Phe Leu Phe Gly Asn Glu Glu Val Lys Val Ser Val Asn
                140                 145                 150

Gly Gln His Phe Leu His Phe Arg Tyr Arg Leu Pro Leu Ser His
                155                 160                 165

Val Asp Thr Leu Gly Ile Phe Gly Asp Ile Leu Val Glu Ala Val
                170                 175                 180

Gly Phe Leu Asn Ile Asn Pro Phe Val Glu Gly Ser Arg Glu Tyr
                185                 190                 195

Pro Ala Gly His Pro Phe Leu Leu Met Ser Pro Arg Leu Glu Val
                200                 205                 210

Pro Cys Ser His Ala Leu Pro Gln Gly Leu Ser Pro Gly Gln Val
                215                 220                 225

Ile Ile Val Arg Gly Leu Val Leu Gln Glu Pro Lys His Phe Thr
                230                 235                 240

Val Ser Leu Arg Asp Gln Ala Ala His Ala Pro Val Thr Leu Arg
                245                 250                 255

Ala Ser Phe Ala Asp Arg Thr Leu Ala Trp Ile Ser Arg Trp Gly
                260                 265                 270

Gln Lys Lys Leu Ile Ser Ala Pro Phe Leu Phe Tyr Pro Gln Arg
                275                 280                 285

Phe Phe Glu Val Leu Leu Leu Phe Gln Glu Gly Gly Leu Lys Leu
                290                 295                 300

Ala Leu Asn Gly Gln Gly Leu Gly Ala Thr Ser Met Asn Gln Gln
                305                 310                 315

Ala Leu Glu Gln Leu Arg Glu Leu Arg Ile Ser Gly Ser Val Gln
                320                 325                 330
```

-continued

Leu Tyr Cys Val His Ser
              335

<210> SEQ ID NO 2
<211> LENGTH: 708
<212> TYPE: PRT
<213> ORGANISM: Homo sapiens
<220> FEATURE: -
<223> OTHER INFORMATION: 2687731

<400> SEQUENCE: 2

Met Lys Asp Met Pro Leu Arg Ile His Val Leu Leu Gly Leu Ala
 1               5                  10                  15

Ile Thr Thr Leu Val Gln Ala Val Asp Lys Lys Val Asp Cys Pro
                20                  25                  30

Arg Leu Cys Thr Cys Glu Ile Arg Pro Trp Phe Thr Pro Arg Ser
                35                  40                  45

Ile Tyr Met Glu Ala Ser Thr Val Asp Cys Asn Asp Leu Gly Leu
                50                  55                  60

Leu Thr Phe Pro Ala Arg Leu Pro Ala Asn Thr Gln Ile Leu Leu
                65                  70                  75

Leu Gln Thr Asn Asn Ile Ala Lys Ile Glu Tyr Ser Thr Asp Phe
                80                  85                  90

Pro Val Asn Leu Thr Gly Leu Asp Leu Ser Gln Asn Asn Leu Ser
                95                  100                 105

Ser Val Thr Asn Ile Asn Val Lys Lys Met Pro Gln Leu Leu Ser
                110                 115                 120

Val Tyr Leu Glu Glu Asn Lys Leu Thr Glu Leu Pro Glu Lys Cys
                125                 130                 135

Leu Ser Glu Leu Ser Asn Leu Gln Glu Leu Tyr Ile Asn His Asn
                140                 145                 150

Leu Leu Ser Thr Ile Ser Pro Gly Ala Phe Ile Gly Leu His Asn
                155                 160                 165

Leu Leu Arg Leu His Leu Asn Ser Asn Arg Leu Gln Met Ile Asn
                170                 175                 180

Ser Lys Trp Phe Asp Ala Leu Pro Asn Leu Glu Ile Leu Met Ile
                185                 190                 195

Gly Glu Asn Pro Ile Ile Arg Ile Lys Asp Met Asn Phe Lys Pro
                200                 205                 210

Leu Ile Asn Leu Arg Ser Leu Val Ile Ala Gly Ile Asn Leu Thr
                215                 220                 225

Glu Ile Pro Asp Asn Ala Leu Val Gly Leu Glu Asn Leu Glu Ser
                230                 235                 240

Ile Ser Phe Tyr Asp Asn Arg Leu Ile Lys Val Pro His Val Ala
                245                 250                 255

Leu Gln Lys Val Val Asn Leu Lys Phe Leu Asp Leu Asn Lys Asn
                260                 265                 270

Pro Ile Asn Arg Ile Arg Arg Gly Asp Phe Ser Asn Met Leu His
                275                 280                 285

Leu Lys Glu Leu Gly Ile Asn Asn Met Pro Glu Leu Ile Ser Ile
                290                 295                 300

Asp Ser Leu Ala Val Asp Asn Leu Pro Asp Leu Arg Lys Ile Glu
                305                 310                 315

Ala Thr Asn Asn Pro Arg Leu Ser Tyr Ile His Pro Asn Ala Phe
                320                 325                 330

```
Phe Arg Leu Pro Lys Leu Glu Ser Leu Met Leu Asn Ser Asn Ala
                335                 340                 345

Leu Ser Ala Leu Tyr His Gly Thr Ile Glu Ser Leu Pro Asn Leu
                350                 355                 360

Lys Glu Ile Ser Ile His Ser Asn Pro Ile Arg Cys Asp Cys Val
                365                 370                 375

Ile Arg Trp Met Asn Met Asn Lys Thr Asn Ile Arg Phe Met Glu
                380                 385                 390

Pro Asp Ser Leu Phe Cys Val Asp Pro Glu Phe Gln Gly Gln
                395                 400                 405

Asn Val Arg Gln Val His Phe Arg Asp Met Met Glu Ile Cys Leu
                410                 415                 420

Pro Leu Ile Ala Pro Glu Ser Phe Pro Ser Asn Leu Asn Val Glu
                425                 430                 435

Ala Gly Ser Tyr Val Ser Phe His Cys Arg Ala Thr Ala Glu Pro
                440                 445                 450

Gln Pro Glu Ile Tyr Trp Ile Thr Pro Ser Gly Gln Lys Leu Leu
                455                 460                 465

Pro Asn Thr Leu Thr Asp Lys Phe Tyr Val His Ser Glu Gly Thr
                470                 475                 480

Leu Asp Ile Asn Gly Val Thr Pro Lys Glu Gly Gly Leu Tyr Thr
                485                 490                 495

Cys Ile Ala Thr Asn Leu Val Gly Ala Asp Leu Lys Ser Val Met
                500                 505                 510

Ile Lys Val Asp Gly Ser Phe Pro Gln Asp Asn Asn Gly Ser Leu
                515                 520                 525

Asn Ile Lys Ile Arg Asp Ile Gln Ala Asn Ser Val Leu Val Ser
                530                 535                 540

Trp Lys Ala Ser Ser Lys Ile Leu Lys Ser Ser Val Lys Trp Thr
                545                 550                 555

Ala Phe Val Lys Thr Glu Asn Ser His Ala Ala Gln Ser Ala Arg
                560                 565                 570

Ile Pro Ser Asp Val Lys Val Tyr Asn Leu Thr His Leu Asn Pro
                575                 580                 585

Ser Thr Glu Tyr Lys Ile Cys Ile Asp Ile Pro Thr Ile Tyr Gln
                590                 595                 600

Lys Asn Arg Lys Lys Cys Val Asn Val Thr Thr Lys Gly Leu His
                605                 610                 615

Pro Asp Gln Lys Glu Tyr Glu Lys Asn Asn Thr Thr Thr Leu Met
                620                 625                 630

Ala Cys Leu Gly Gly Leu Leu Gly Ile Ile Gly Val Ile Cys Leu
                635                 640                 645

Ile Ser Cys Leu Ser Pro Glu Met Asn Cys Asp Gly Gly His Ser
                650                 655                 660

Tyr Val Arg Asn Tyr Leu Gln Lys Pro Thr Phe Ala Leu Gly Glu
                665                 670                 675

Leu Tyr Pro Pro Leu Ile Asn Leu Trp Glu Ala Gly Lys Glu Lys
                680                 685                 690

Ser Thr Ser Leu Lys Val Lys Ala Thr Val Ile Gly Leu Pro Thr
                695                 700                 705

Asn Met Ser
```

<210> SEQ ID NO 3
<211> LENGTH: 1643
<212> TYPE: DNA
<213> ORGANISM: Homo sapiens
<220> FEATURE: -
<223> OTHER INFORMATION: 2635136

<400> SEQUENCE: 3

| | |
|---|---|
| tgcaatggcc atatgctgca gacccggagt gggtagttag ttggttaatg ccagtcttcc | 60 |
| tcccctggac actgagttct gctgacagcc cccgcccagc cagagctctg ctgtatacca | 120 |
| ccgggagtgg ggctggtgtg gagcctggag gtcgcccgct gccctcctag ggctgctcca | 180 |
| gacagcatta aaacgctgca ggtcgcaggt gagactaaca gctgggagag ctgctccagg | 240 |
| catttaggac cctgactggg gcagatgagt cagcccagtg ggggcagggc tcctggaacg | 300 |
| aggatctaca gttggagttg ccccactgtc atgtcacctg gagaaaaact ggacccaatt | 360 |
| cctgacagct tcattctgca accaccagtc ttccacccgg tggttcctta tgtcacgacg | 420 |
| atttttggag gcctgcatgc aggcaagatg gtcatgctgc aaggagtggt ccctctagat | 480 |
| gcacacaggt ttcaggtgga cttccagtgt ggctgcagcc tgtgtccccg ccagatatc | 540 |
| gccttccact tcaaccctcg cttccatacc accaagcccc atgtcatctg caacaccctg | 600 |
| catggtggac gctggcaaag ggaggcccgg tggccccacc tggccctgcg aagaggctcc | 660 |
| agcttcctca tcctctttct cttcgggaat gaggaagtga aggtgagtgt gaatggacag | 720 |
| cactttctcc acttccgcta ccggctccca ctgtctcatg tggacacgct gggtatattt | 780 |
| ggtgacatcc tggtagaggc tgttggattc ctgaacatca atccatttgt ggagggcagc | 840 |
| agagagtacc cagctggaca tcctttcctg ctgatgagcc caggctgga ggtgccctgc | 900 |
| tcacatgctc ttcccccaggg tctctcgcct gggcaggtca tcatagtacg gggactggtc | 960 |
| ttgcaagagc cgaagcattt tactgtgagc ctgagggacc aggctgccca tgctcctgtg | 1020 |
| acactcaggg cctccttcgc agacagaact ctggcctgga tctcccgctg ggggcagaag | 1080 |
| aaactgatct cagccccctt cctcttttac ccccagagat tctttgaggt gctgctcctg | 1140 |
| ttccaggagg gagggctgaa gctggcgctc aatgggcagg ggctggggc caccagcatg | 1200 |
| aaccagcagg ccctggagca gctgcgggag ctccggatca gtggaagtgt ccagctctac | 1260 |
| tgtgtccact cctgaggatg gttccaggga ataccgcca gaaaacaaga aggtcagccc | 1320 |
| actcccaggg ccccactctc ctcccctcat taaaccatcc acctgacacc agcacatcag | 1380 |
| gcctggttca cctctggggt cacgagactg agtctacagg agctttgggc ctgagggaag | 1440 |
| gcacaagagt gcaaaggttc ctcgaactct gcaccttcct ccaccaggag cctgggatat | 1500 |
| ggctccatct gccttcaggg cctggactgc actcacagag gcaagtgttg tagactaaca | 1560 |
| aagatactcc aaaatacaat ggcttaaaga atgtggtcat ttattcttta ttatttattt | 1620 |
| atttgtggtc aaataaataa ata | 1643 |

<210> SEQ ID NO 4
<211> LENGTH: 2290
<212> TYPE: DNA
<213> ORGANISM: Homo sapiens
<220> FEATURE: -
<223> OTHER INFORMATION: 2687731

<400> SEQUENCE: 4

| | |
|---|---|
| cttactagca ctgactgtgg aatccttaag ggcccattac atttctgaag aagaaagcta | 60 |
| agatgaagga catgccactc cgaattcatg tgctacttgg cctagctatc actacactag | 120 |

-continued

```
tacaagctgt agataaaaaa gtggattgtc cacggttatg tacgtgtgaa atcaggcctt      180
ggtttacacc cagatccatt tatatggaag catctacagt ggattgtaat gatttaggtc      240
ttttaacttt cccagccaga ttgccagcta acacacagat tcttctccta cagactaaca      300
atattgcaaa aattgaatac tccacagact ttccagtaaa ccttactggc ctggatttat      360
ctcaaaacaa tttatcttca gtcaccaata ttaatgtaaa aaagatgcct cagctccttt      420
ctgtgtacct agaggaaaac aaacttactg aactgcctga aaaatgtctg tccgaactga      480
gcaacttaca agaactctat attaatcaca acttgctttc tacaatttca cctggagcct      540
ttattggcct acataatctt cttcgacttc atctcaattc aaatagattg cagatgatca      600
acagtaagtg gtttgatgct cttccaaatc tagagattct gatgattggg gaaaatccaa      660
ttatcagaat caaagacatg aactttaagc ctcttatcaa tcttcgcagc ctggttatag      720
ctggtataaa cctcacagaa ataccagata acgccttggt tggactggaa aacttagaaa      780
gcatctcttt ttacgataac aggcttatta agtacccca tgttgctctt caaaaagttg       840
taaatctcaa atttttggat ctaaataaaa atcctattaa tagaatacga aggggtgatt      900
ttagcaatat gctacactta aaagagttgg ggataaataa tatgcctgag ctgatttcca      960
tcgatagtct tgctgtggat aacctgccag atttaagaaa aatagaagct actaacaacc     1020
ctagattgtc ttacattcac cccaatgcat ttttcagact ccccaagctg aatcactca      1080 tgctgaacag caatgctctc agtgccctgt accatggtac cattgagtct ctgccaaacc     1140
tcaaggaaat cagcatacac agtaaccccca tcaggtgtga ctgtgtcatc cgttggatga     1200
acatgaacaa aaccaacatt cgattcatgg agccagattc actgttttgc gtggacccac     1260
ctgaattcca aggtcagaat gttcggcaag tgcatttcag ggacatgatg gaaatttgtc     1320
tccctcttat agctcctgag agctttcctt ctaatctaaa tgtagaagct gggagctatg     1380
tttcctttca ctgtagagct actgcagaac cacagcctga aatctactgg ataacacctt     1440
ctggtcaaaa actcttgcct aatacctga cagacaagtt ctatgtccat tctgagggaa      1500
cactagatat aaatggcgta actcccaaag aaggggggttt atatacttgt atagcaacta     1560
acctagttgg cgctgacttg aagtctgtta tgatcaaagt ggatggatct tttccacaag     1620
ataacaatgg ctctttgaat attaaaataa gagatattca ggccaattca gttttggtgt     1680
cctggaaagc aagttctaaa attctcaaat ctagtgttaa atggacagcc tttgtcaaga     1740
ctgaaaattc tcatgctgcg caaagtgctc gaataccatc tgatgtcaag gtatataatc     1800
ttactcatct gaatccatca actgagtata aaatttgtat tgatattccc accatctatc     1860
agaaaaacag aaaaaaatgt gtaaatgtca ccaccaaagg tttgcaccct gatcaaaaag     1920
agtatgaaaa gaataatacc acaacactta tggcctgtct tggaggcctt ctggggatta     1980
ttggtgtgat atgtcttatc agctgcctct ctccagaaat gaactgtgat ggtggacaca     2040
gctatgtgag gaattactta cagaaaccaa cctttgcatt aggtgagctt tatcctcctc     2100
tgataaatct ctgggaagca ggaaaagaaa aagtacatc actgaaagta aaagcaactg      2160
ttataggttt accaacaaat atgtcctaaa aaccaccaag gaaacctact ccaaaaatga     2220
acaaaaaaaa aaaagcgaa agactgcagt tgtgctaaaa acaaaacaaa acaaacaaac     2280
aaaaaaaaaa                                                           2290
```

<210> SEQ ID NO 5
<211> LENGTH: 316
<212> TYPE: PRT
<213> ORGANISM: Homo sapiens -continued

```
<220> FEATURE: -
<223> OTHER INFORMATION: g1932712

<400> SEQUENCE: 5

Met Leu Ser Leu Asn Asn Leu Gln Asn Ile Ile Tyr Asn Pro Val
 1               5                  10                  15

Ile Pro Phe Val Gly Thr Ile Pro Asp Gln Leu Asp Pro Gly Thr
                 20                  25                  30

Leu Ile Val Ile Arg Gly His Val Pro Ser Asp Ala Asp Arg Phe
                 35                  40                  45

Gln Val Asp Leu Gln Asn Gly Ser Ser Val Lys Pro Arg Ala Asp
                 50                  55                  60

Val Ala Phe His Phe Asn Pro Arg Phe Lys Arg Ala Gly Cys Ile
                 65                  70                  75

Val Cys Asn Thr Leu Ile Asn Glu Lys Trp Gly Arg Glu Glu Ile
                 80                  85                  90

Thr Tyr Asp Thr Pro Phe Lys Arg Glu Lys Ser Phe Glu Ile Val
                 95                 100                 105

Ile Met Val Leu Lys Asp Lys Phe Gln Val Ala Val Asn Gly Lys
                110                 115                 120

His Thr Leu Leu Tyr Gly His Arg Ile Gly Pro Glu Lys Ile Asp
                125                 130                 135

Thr Leu Gly Ile Tyr Gly Lys Val Asn Ile His Ser Ile Gly Phe
                140                 145                 150

Ser Phe Ser Ser Asp Leu Gln Ser Thr Gln Ala Ser Ser Leu Glu
                155                 160                 165

Leu Thr Glu Ile Val Arg Glu Asn Val Pro Lys Ser Gly Thr Pro
                170                 175                 180

Gln Leu Ser Leu Pro Phe Ala Ala Arg Leu Asn Thr Pro Met Gly
                185                 190                 195

Pro Gly Arg Thr Val Val Gln Gly Glu Val Asn Ala Asn Ala
                200                 205                 210

Lys Ser Phe Asn Val Asp Leu Leu Ala Gly Lys Ser Lys Asp Ile
                215                 220                 225

Ala Leu His Leu Asn Pro Arg Leu Asn Ile Lys Ala Phe Val Arg
                230                 235                 240

Asn Ser Phe Leu Gln Glu Ser Trp Gly Glu Glu Arg Asn Ile
                245                 250                 255

Thr Ser Phe Pro Phe Ser Pro Gly Met Tyr Phe Glu Met Ile Ile
                260                 265                 270

Tyr Cys Asp Val Arg Glu Phe Lys Val Ala Val Asn Gly Val His
                275                 280                 285

Ser Leu Glu Tyr Lys His Arg Phe Lys Glu Leu Ser Ser Ile Asp
                290                 295                 300

Thr Leu Glu Ile Asn Gly Asp Ile His Leu Leu Glu Val Arg Ser
                305                 310                 315

Trp
```